(12) United States Patent
Nanduri et al.

(10) Patent No.: US 8,527,056 B2
(45) Date of Patent: Sep. 3, 2013

(54) ENCODING OF SIZE AND BRIGHTNESS OF PERCEPTS IN A VISUAL PROSTHESIS

(75) Inventors: Devyani Nanduri, Los Angeles, CA (US); Mark S. Humayun, Glendale, CA (US); James D. Weiland, Valencia, CA (US); Jessy Dorn, Los Angeles, CA (US); Robert J. Greenberg, Los Angeles, CA (US); Ione Fine, Seattle, WA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 124 days.

(21) Appl. No.: 13/097,534

(22) Filed: Apr. 29, 2011

(65) Prior Publication Data

US 2011/0270352 A1    Nov. 3, 2011

Related U.S. Application Data

(60) Provisional application No. 61/334,459, filed on May 13, 2010, provisional application No. 61/356,500, filed on Jun. 18, 2010, provisional application No. 61/330,109, filed on Apr. 30, 2010.

(51) Int. Cl.
*A61N 1/00* (2006.01)

(52) U.S. Cl.
USPC ............................................. 607/53

(58) Field of Classification Search
USPC ............................................. 607/53
See application file for complete search history.

(56) References Cited

U.S. PATENT DOCUMENTS

| | | | |
|---|---|---|---|
| 5,109,844 A | 5/1992 | de Juan, Jr. et al. | |
| 5,935,155 A | 8/1999 | Humayun et al. | |
| 6,400,989 B1 | 6/2002 | Eckmiller | |
| 6,458,157 B1 | 10/2002 | Suaning | |
| 7,574,263 B2 * | 8/2009 | Greenberg et al. | 607/54 |

* cited by examiner

*Primary Examiner* — George Manuel
(74) *Attorney, Agent, or Firm* — Scott B. Dunbar; Gary Schnittgrund

(57) ABSTRACT

Methods of electrically stimulating percepts in a patient with a visual prosthesis are discussed. Changes in amplitude of stimulation increase both the perceived brightness and the perceived size of the precept. Changes in frequency of stimulation change the perceived brightness without altering the perceived size of the percept. Hence, a source image may be mapped to a combination of amplitude and frequency that best induces the desired image.

20 Claims, 9 Drawing Sheets

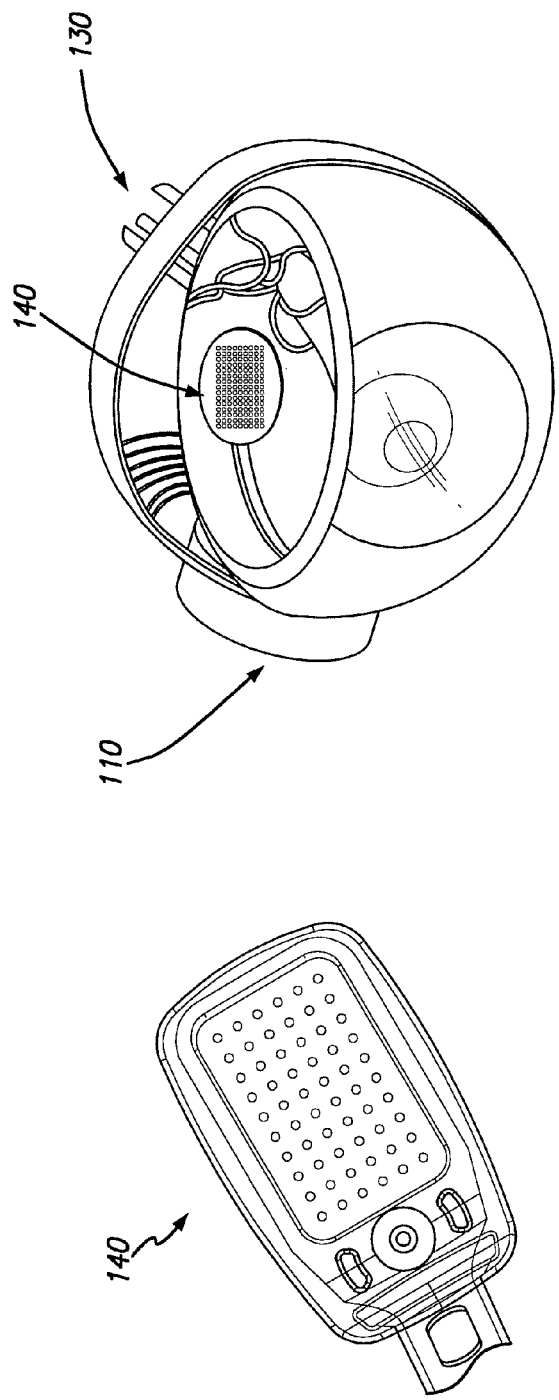
FIG. 1A
FIG. 1B
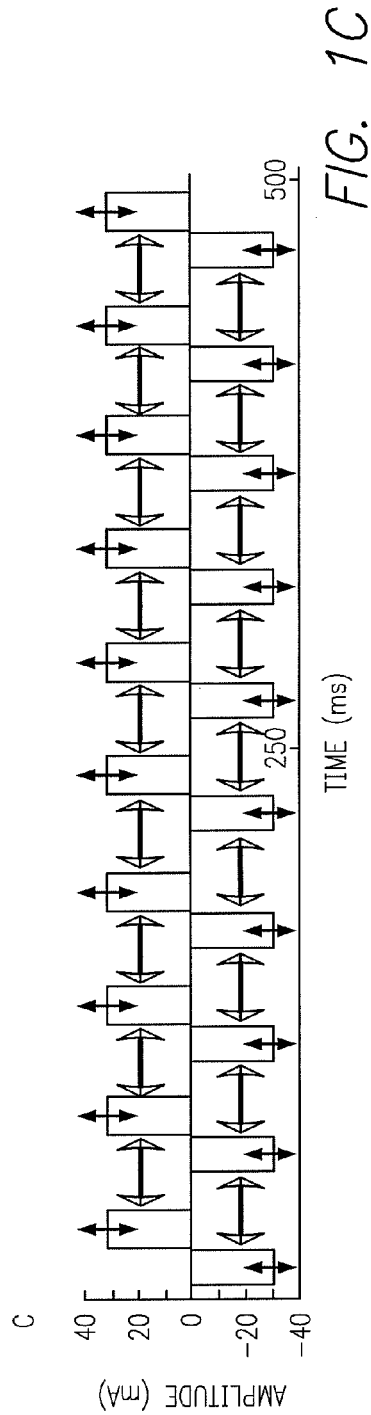
FIG. 1C

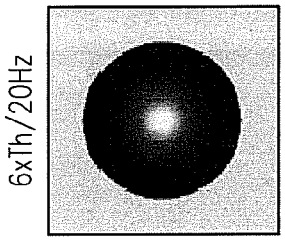
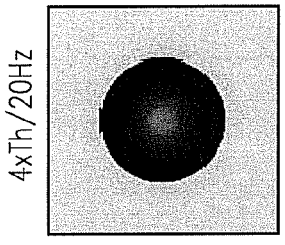
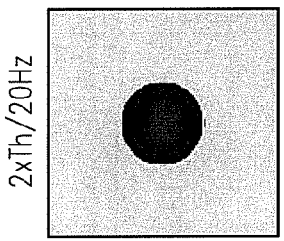
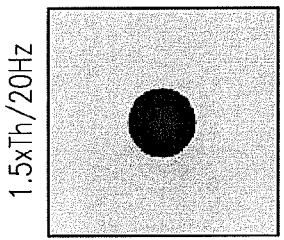
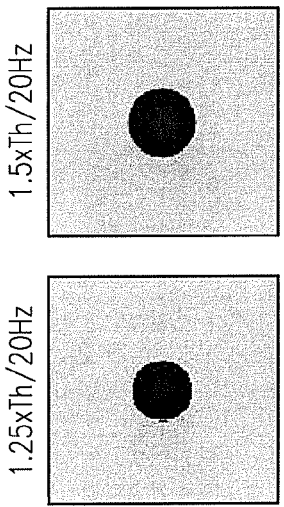
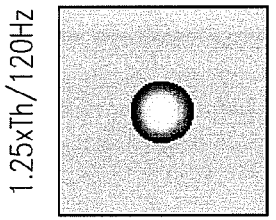
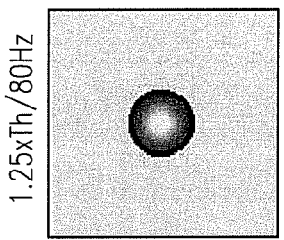
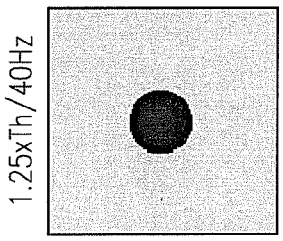
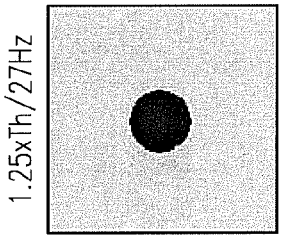
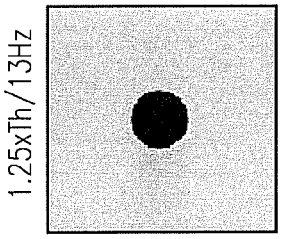

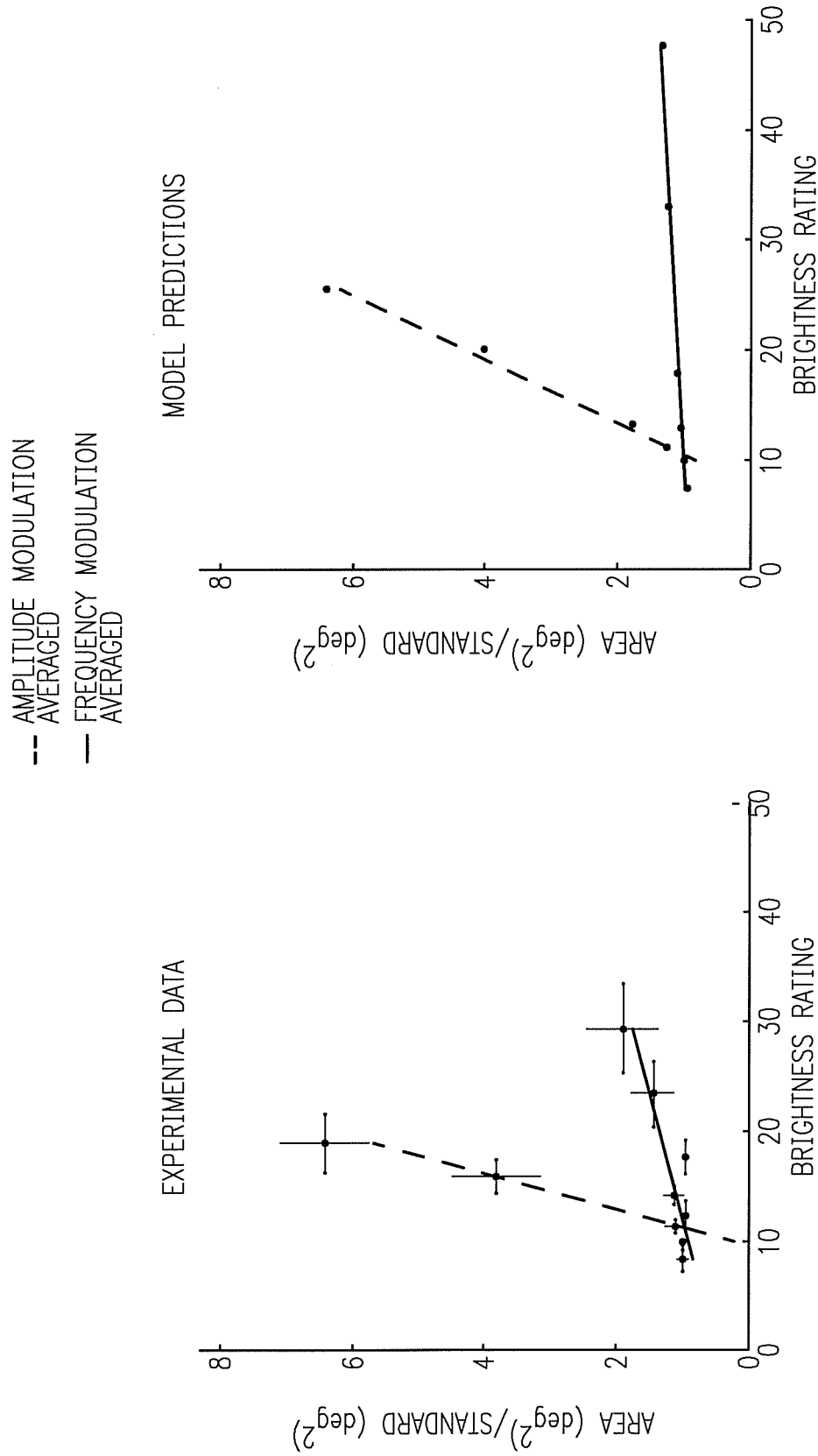

ENCODING OF SIZE AND BRIGHTNESS OF PERCEPTS IN A VISUAL PROSTHESIS

CROSS REFERENCE TO RELATED APPLICATIONS

The present application claims priority to U.S. Provisional Application No. 61/334,459 entitled "Manipulation of Frequency and Amplitude have Separable Effects on the Size and Brightness of Percepts in a Retinal Prosthesis Subject", filed on May 13, 2010, U.S. Provisional Application No. 61/356,500 entitled "Frequency Encoding of Brightness for Phosphene Size Control", filed on Jun. 18, 2010, and U.S. Provisional Application No. 61/330,109 entitled "Shape Analysis for Fitting in a Visual Prosthesis", filed on Apr. 30, 2010, the disclosures of which are incorporated herein by reference in their entirety.

The present application may be related to U.S. patent application Ser. No. 12/548,275 entitled "System and Method for Measuring and Fitting Spatio-Temporal Vision", filed on Aug. 26, 2009 and U.S. patent application Ser. No. 11/818,373 entitled "Apparatus and Method for Electrical Stimulation of Human Retina", filed on Jun. 14, 2007, the disclosures of which are incorporated herein by reference in its entirety. The present application may be further related to U.S. Pat. No. 6,920,358, granted Jul. 19, 2005, entitled "Video Processing Methods for Improving Visual Acuity and/or Perceived Image Resolution", U.S. Pat. No. 7,574,263, granted Aug. 11, 2009, entitled "Pixel Re-Mapping for Visual Prosthesis", U.S. Pat. No. 7,483,751, granted Jan. 27, 2009, entitled "Automatic Fitting for a Visual Prosthesis", and U.S. Pat. No. 7,738,962, granted Jun. 15, 2000, entitled "Fitting of Brightness in a Visual Prosthesis", the disclosures of which are incorporated herein by reference in their entirety.

The present application is also related to U.S. patent application entitled "Shape Analysis for Fitting in a Visual Prosthesis", Ser. No. 13/097,516 filed on even date herewith, the disclosure of which is incorporated herein by reference in its entirety.

STATEMENT OF GOVERNMENT GRANT

This invention was made with government support under grant No. R24EY12893-01, awarded by the National Institutes of Health. The government has certain rights in the invention.

FIELD

The present disclosure is generally directed to neural stimulation and more specifically to an encoding of size and brightness of percepts in a visual prosthesis.

BACKGROUND

Neural tissue can be artificially stimulated and activated by prosthetic devices that pass pulses of electrical current through electrodes on the prosthetic devices. The passage of current causes changes in electrical potentials across visual neuronal membranes, which can initiate visual neuron action potentials. These visual neuron action potentials are the means of information transfer in the nervous system.

Based on this mechanism, it is possible to input information into the nervous system by coding sensory information as a sequence of electrical pulses relayed to the nervous system via a prosthetic device. In this way, it is possible to provide artificial sensations including vision.

One typical application of neural tissue stimulation is in rehabilitation of the blind. Some forms of blindness involve selective loss of light sensitive transducers of the retina. Other retinal neurons remain viable, however, and may be activated in the manner described above by placement of a prosthetic electrode device on the inner (toward the vitreous) retinal surface (epiretinal). This placement should be mechanically stable, minimize distance between the prosthetic device electrodes and the visual neurons, control electronic field distribution and avoid undue compression of the visual neurons.

Each person's response to neural stimulation differs. In the case of retinal stimulation, even a single person's response may vary from one region of the retina to another. In general, the retina is more sensitive closer to the fovea. Also worth noting for neural stimulation is that stimulation less than a minimum threshold value would be ineffective in eliciting perception. On the other hand, stimulation beyond a maximum level would be painful and possibly dangerous to a patient. It is therefore important to map any video image to a stimulation range between a minimum and a maximum for each individual electrode. With a simple retinal prosthesis with only one or very few electrodes, it is possible to adjust the stimulation manually by stimulating and questioning the patient.

The human retina includes about four million individual photoreceptors. An effective visual prosthesis may include thousands of electrodes or more. As resolution and number of electrodes increase, it may become difficult to adjust each electrode separately by stimulating and eliciting a patient response. Therefore, a system is needed to adjust the electrodes in a visual prosthesis with multiple electrodes for size, brightness and shape of percepts without need for patient interaction in a possibly long and difficult process of characterizing each electrode individually.

SUMMARY

According to a first aspect, a method of stimulating perception of vision with a visual prosthesis is disclosed. The method of stimulating perception of vision with a visual prosthesis comprising adjusting percept size by adjusting amplitude of a stimulation signal of at least one electrode of the visual prosthesis.

According to a second aspect, a method for adjusting size and brightness of a percept independently is disclosed. The method for adjusting size and brightness of a percept independently comprising: providing a visual prosthesis with at least one electrode; stimulating the at least one electrode with a pulsed electrical signal to elicit a percept; adjusting amplitude of the pulsed electrical signal applied to the at least one electrode and measuring resulting percept size and brightness; adjusting frequency of the pulsed electrical signal applied to the at least one electrode and measuring resulting percept size and brightness; deriving a model of the resulting percept size and brightness from the adjusting of amplitude and frequency; and utilizing the model to adjust the amplitude and frequency of the pulsed electrical signal for stimulating the at least one electrode to elicit a percept of controlled size and brightness.

According to a third aspect a visual prosthesis is disclosed. The visual prosthesis comprising: a neural stimulator, adapted for applying stimuli to visual neural tissue to elicit percepts; a control device, coupled to the neural stimulator and adapted for controlling amplitude of the stimuli, and controlling frequency of the stimuli independently of the amplitude of the stimuli and a computing device, coupled to the control device and adapted for deriving a model for size and brightness of each percept as a function of the amplitude and frequency of the stimuli; wherein the control device is further adapted for adjusting the amplitude and frequency of the stimuli based on the model to elicit at least one percept of an expected size and brightness.

According to a fourth aspect, a device is disclosed. The device for controlling a visual prosthesis, comprising: means for controlling amplitude and frequency of stimuli to be applied to visual neural tissue by the visual prosthesis; means for deriving a model for adjusting the amplitude and frequency of the stimuli based on desired percept size and brightness; and means for applying the model to adjust the amplitude and frequency of the stimuli to be applied based on the desired percept size and brightness.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 1A shows an exemplary 6×10 electrode array of a retinal prosthesis.

FIG. 1B shows a perspective view of an exemplary implanted portion of a retinal prosthesis.

FIG. 1C shows an exemplary series of pulse trains that can be modulated in frequency and amplitude.

FIG. 4A shows brightness plotted as a function of amplitude. FIG. 4B shows brightness plotted as a function of frequency. FIG. 4C shows size plotted as a function of amplitude. FIG. 4D shows size plotted as a function of frequency.

FIGS. 6A-6K show an exemplary series of percepts as predicted by a model for increasing amplitude (FIGS. 6A through 6E) and increasing frequency (FIGS. 6F through 6K)

FIG. 7A shows an exemplary graph showing experimental results of average area and brightness of percepts at various amplitudes and frequencies of stimulation. FIG. 7B shows an exemplary graph showing modeling predictions for average area and brightness of percepts at various amplitudes and frequencies of stimulation, the model derived by the results shown in FIG. 7A.

DETAILED DESCRIPTION

Figure 2:
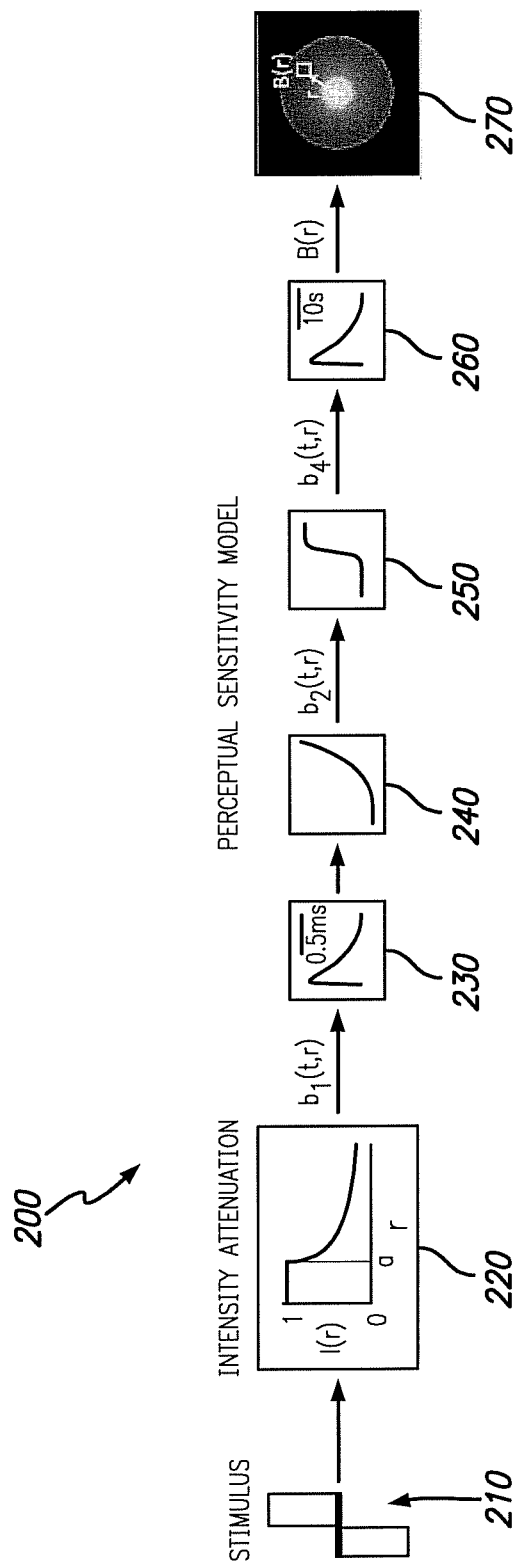
FIG. 2 shows a schematic view of an exemplary method for deriving a model, according to an embodiment of the present disclosure

The present disclosure describes methods for electrically stimulating percepts in a patient using a visual prosthesis. Changes in amplitude of stimulation increase perceived size of the percept with a small change in perceived brightness. Changes in frequency of stimulation change the perceived brightness without significantly altering the perceived size of the percept. A spatial sensitivity model is developed to quantify change in size and brightness of the percept as a function of the amplitude and frequency of the stimulation. Hence, a source image may be mapped to a combination of amplitude and frequency that best induces a desired image.

One method for using frequency coding for a visual prosthesis (one that stimulates retina, lateral geniculate nucleus, visual cortex, etc.) would be to map pixel intensity to a corresponding frequency of stimulation on an electrode. Thus, for the same number of input pixel intensities as electrodes, there would be a one-to-one map between intensity and frequency of stimulation such that increasing brightness would result in higher frequency of stimulation on the corresponding electrode. This relationship may be linear, logarithmic, exponential, or any other function, but output frequency will monotonically increase with input pixel brightness. Typically the amplitude and pulse durations would be held constant in this frequency-modulated prosthesis, but that is not required—e.g., amplitude and/or pulse durations could be simultaneously varied to produce a combined effect since total charge per time is related to brightness as described in U.S. patent application Ser. No. 11/818,373.

In the case where there are more pixel intensities than electrodes (e.g., input video camera is of a higher resolution than the electrode array), the image can first be processed to reduce image pixel count to be equal to electrode count.

The term "phosphene" is used interchangeably with "percept" throughout the present disclosure and is defined as perception of a visual image created by electrical stimulation of visual neural tissue such as retinal tissue.

A visual prosthesis system is generally used to create a two-dimensional array of phosphenes in visual space that forms an accurate spatial representation of visual scenes in the world. The visual prosthesis system can be, for instance, an epiretinal prosthesis system for stimulation of the retina. In the ideal situation, vision would be restored by taking an image seen in the visual field of a video camera, pixelating the image to the resolution of the array, and then representing each of these pixels by an individual phosphene that can vary in brightness. The result would be an image much like a gray-scale digital scoreboard. For this to be successful, the phosphenes created by electrically stimulating a region of the retina with a single electrode would preferrably behave like independent pixels across a range of brightness levels.

Applicants performed a series of experiments quantifying relationship between stimulation and percept for a single electrode or pair of electrodes. Results of these experiments have shown that perceptual thresholds are influenced by proximity of the electrodes to the retina surface, as shown in references 1 and 2 (each of which is incorporated herein by reference in its entirety), and that both threshold and brightness for a single electrode or pair of electrodes can be predicted across a variety of parameters such as frequency, pulse duration and amplitude. as shown in reference 3 (incorporated herein by reference in its entirety).

In particular, it has been shown that increases in both current amplitude and stimulation frequency result in greater percept brightness (see references 3 and 4, which are incorporated herein by reference in their entirety). However, prior studies examining this relationship relied primarily on either threshold or brightness matching judgments and did not examine how shape of elicited percepts varies as a function of stimulus amplitude and frequency (see references 5, which is incorporated herein by reference in its entirety). Previous clinical visual prosthesis studies reporting on phosphene shape information were largely anecdotal, did not systematically repeat multiple trials for a given stimulus and did not compare percepts produced from a variety of stimuli, as shown in references 6 through 10 (each of which is incorporated herein by reference in its entirety).

Applicants have performed a series of experiments to test whether modulating amplitude or frequency changed properties of percept appearance in different ways. The If amplitude and frequency have separable effects on percept size, it can be possible to develop stimulation protocols for encoding visual images that can independently manipulate the size and brightness of phosphenes, thereby increasing flexibility of possible range of percepts that can be elicited.

Applicants have found that increasing of stimulation amplitude generally increased the size and often increased the brightness of the elicited phosphene. On most electrodes, increasing stimulation frequency generally increased only brightness while having a negligible effect on the percept size. Experimental findings are reproducible with a computational model based on the visual sensitivity properties of the retina and the spatial spread of current from a disk electrode.

As with any system, there are several engineering constraints which may limit the capabilities of the device, such as, in the present case, electrode size, charge density limit and electrode retina distance, as shown in reference 2. Working under these constraints, a successful retinal prosthesis can utilize a stimulation paradigm that optimizes available resolution and contrast to present the visual world to patients. Based on the Applicants' findings with frequency coding, Applicants can maintain system resolution across varying degrees of contrast. For a particular subject, the array is implanted in the macular region with electrodes in contact with the retina. As shown in references 11 and 12 (each of which is incorporated herein by reference in its entirety), phosphene properties can be studied in regions where progression of retinal pigmentosa (RP) is known to be more severe, such as in the extramacular retina Amplitude coding can be more effective in the extramacular region since ganglion cell density is lower and receptive fields are larger and presumably less sensitive to stimulation. If a wider array can be realized that can stimulate central and peripheral retina, then it may be advantageous to use frequency coding within the macular region for better resolution and amplitude coding in the periphery.

Ideally, a retinal prosthesis provides electrical stimulation patterns that optimize the representation of the visual world. Applicants can use a computational model to generate predictable stimulation paradigms with higher contrast that would be of benefit to the patient. This type of computational module can be utilized in a visual prosthesis to form perception capabilities at higher resolution. Such computational module can be utilized in conjunction with other enhancements of perception capabilities such as the shape fitting described in the copending U.S. patent application entitled "Shape Analysis for Fitting in a Visual Prosthesis" filed on even date herewith.

FIG. 1A shows an exemplary 6×10 flexible circuit electrode array of a retinal prosthesis. Even though a 6×10 array is shown, the electrode array can have more or fewer electrodes for higher or lower resolution, respectively.

FIG. 1B shows a perspective view of an exemplary implanted portion of a retinal prosthesis. The retinal prosthesis comprises a flexible circuit electrode array 140 mounted by a retinal tack (not shown) or similar means to the epiretinal surface and can be near an optic nerve 130. The flexible circuit electrode array 140 is electrically coupled to an electronics package 110 which may comprise neroustimulator(s) and control device(s).

FIG. 1C shows a plot of an exemplary biphasic pulse train stimulus for eliciting percepts with the visual prosthesis. These pulse trains can be modulated by either changing pulse amplitude (shown with solid arrows) or pulse frequency (shown with hollow arrows).

FIG. 2 shows a schematic view of an exemplary method for deriving a spatial sensitivity model 200, according to an embodiment of the present disclosure. A temporal input stimulus pulse train 210, f(t), is transformed into a spatio-temporal representation 230 based on a spatial attenuation function 220 from an electrode. Output of the a spatial attenuation function 220 is convolved with a temporal low-pass filter with a one-stage gamma function with a time constant $\tau 1=0.42$ ms as its impulse response.

Applicants then assume that the system becomes less sensitive as a function of accumulated charge by calculating the amount of accumulated cathodic charge over time, and convolving this accumulation with a second one-stage gamma function with time constant $\tau 2=45.25$ ms 230. The output of this convolution, is scaled (by a factor $\epsilon=8.73$), and subtracted from the output of the first convolution.

The resulting time course is half-rectified 240 then passed through a sigmoidal function 250 and passed through a power non-linearity at $\beta=0.8$. Finally, as in the pre-existing Perceptual Sensitivity Model, the output, b4$(t, r)$ is convolved with a low-pass filter described using a three-stage gamma function with time constant $\tau 3=26.25$ ms. as a slow integrator stage 260. The resulting output corresponds to a spatial brightness response 270, B(r).

According to many embodiments of the present disclosure, the spatial sensitivity model 200, as shown in FIG. 2, can be shown to be capable of determining the size and spatial brightness of a phosphene resulting from pulse train stimulation of the retina with an electrode. This model 200 is based on combining previous work that predicted the perceptual sensitivity of the retina due to electrical stimulation in human subjects, shown in reference 3, and the spread of current from a metal disk in a semi-infinite medium based on electrophysiological spatial threshold data shown, for instance, in reference 13 (incorporated herein by reference in its entirety).

The Perceptual Sensitivity Model as described in references 14-17 (each of which is incorporated herein by reference in its entirety), takes a stimulus pulse train and passes it through a series of filters, each filter comparable to a different stage in temporal visual integration, to predict if the stimulus yields a percept. While filter time constants ($\tau_1, \tau_2, \tau_3$) do not change from threshold to suprathreshold stimulation, desensitization as a result of accumulated charge ($\epsilon$) and power input-output nonlinearity ($\beta$) differ from threshold to suprathreshold stimulation.

In a first stage of the Applicants' spatial sensitivity model 200, as shown in FIG. 2, Applicants apply the spatial attenuation function 220 to the temporal input stimulus pulse train 210 to produce $b_1(t,r)$, a spatio-temporal stimulus profile 230 given by:

$$b_1(t,r) = f(t)I(r) \tag{1}$$

where f(t) is the electrical stimulation input pattern, t is the time (in milliseconds), r is the distance from the center of the stimulating electrode in microns and I(r) is the current attenuation from a disc electrode. The function used to model the spatial attenuation of current is given by:

$$I(r) = \begin{cases} \dfrac{14000}{14000 + (r-a)^{1.69}} & r > a \\ 1 & r \leq a \end{cases} \quad (2)$$

where r is the distance from the center of the stimulating disc electrode and a is the radius of the electrode.

In a second stage of the spatial sensitivity model 200, Applicants pass the spatiotemporal stimulus profile through the Perceptual Sensitivity Model. Model parameters were based on filter time constants, suprathreshold desensitization and power non-linearity parameters ($\tau_1$=0.42, $\tau_2$=45.25, $\tau_3$=26.25, $\epsilon$=8.73 and $\beta$=0.8) with a minor modification to account for the varying $\beta$ from threshold to suprathreshold. In reference 3, the output after the second convolution and desensitization was placed through a power non-linearity of either $\beta$=3.4 at threshold and $\beta$=0.8 at suprathreshold. In the Applicants' spatial sensitivity model 200, the effects of threshold ($\beta$=3.4) are substituted by a sigmoidal function, which (analogous to the Perceptual Sensitivity Model) has an accelerating nonlinearity near threshold and a compressive nonlinearity at suprathreshold.

Specifically, Applicants first input $b_1(t,r)$ through the first two stages 230 and 240 of the Perceptual Sensitivity Model (current integration with $\tau_1$=0.42 and desensitization with $\tau_2$=45.25, $\epsilon$=8.73) to yield $b_2(t,r)$. Then $b_2(t,r)$ is passed through a sigmoidal function 250 S(r) and power non-linearity with $\beta$=0.8. The result is given by:

$$b_4(t,r) = [|b_2(t,r)|]^\beta S(r) \quad (3)$$

where S(r) is given by:

$$S(r) = \dfrac{A}{1 + e^{\frac{C-b_4(r)}{D}}} \text{ and } b_3(r) = \max[b_2(t,r)]$$

The output, $b_4(r)$, is then passed through the slow integrator stage 260 of the Perceptual Sensitivity Model ($\tau_3$=26.25). The maximum value of the output from the slow integrator 260 represents the brightness response in space B(r). This is then translated to an x-y coordinate system to yield a full spatial representation 270 ($x^2+y^2=r^2$, |x|<2000 µm |y|<2000 µm). Note that Perceptual Sensitivity Model assumes an electrode disk is placed at the origin. For a given stimulus, the brightness of a phosphene is calculated as the maximum brightness of the B(r) plot, while size is determined by the area of B(r)>$\Theta$, where $\Theta$ is a constant representing the minimum brightness value of a visible percept.

Figure 3A:
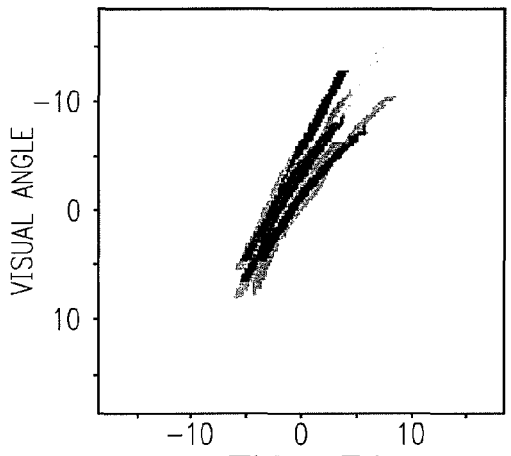
FIGS. 3A-3F show an exemplary series of graphs recording shape of the percept or phosphene under standard stimulation conditions (FIGS. 3A and 3B), increased amplitude conditions (FIGS. 3C and 3D), and increased frequency conditions (FIGS. 3E and 3F).
Figure 3B:
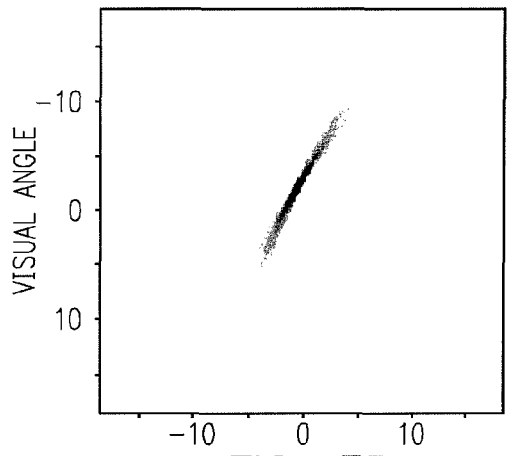
Figure 3C:
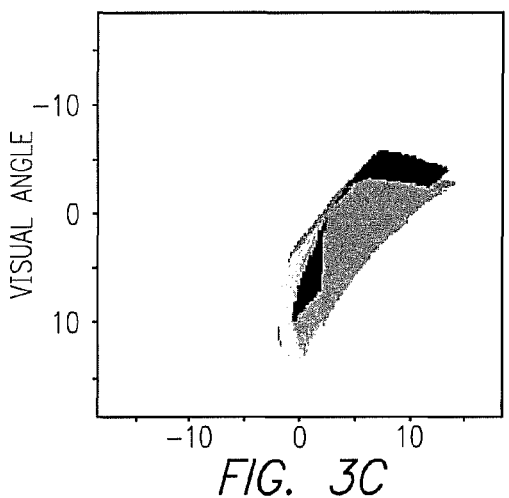
Figure 3D:
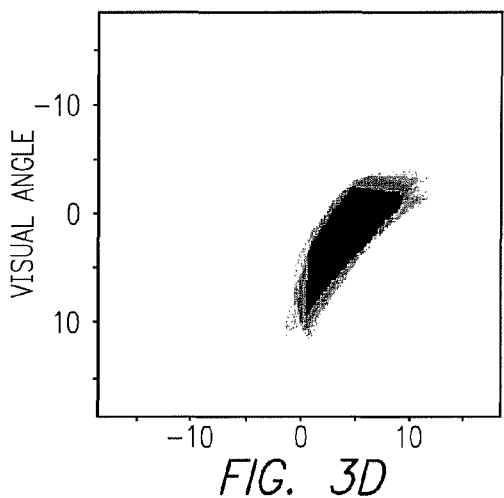
Figure 3E:
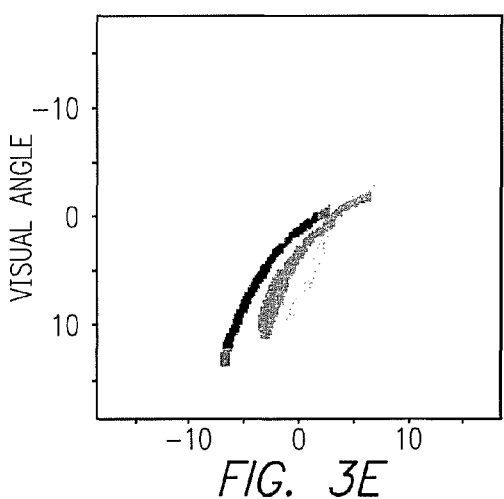
Figure 3F:
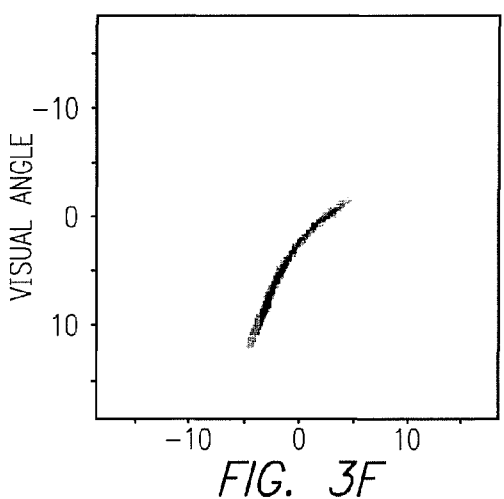

FIGS. 3A-3F show an exemplary series of graphs recording shape of the perceived image or percept under standard stimulation conditions (FIGS. 3A and 3B), higher amplitude conditions (FIGS. 3C and 3D), and higher frequency conditions (FIGS. 3E and 3F). Specifically, FIG. 3A shows ten trials for the same single electrode as FIG. 3B at 1.25×Th/20 Hz, FIG. 3B shows average of the ten trials from FIG. 3A, FIG. 3C shows five trials at 4×Th/20 Hz, FIG. 3D shows average of the five trials from FIG. 3C, FIG. 3E shows five trials at 1.25×Th/80 Hz, and FIG. 3F shows average of the five trials from FIG. 3E. Th is noted as the threshold value for amplitude and frequency to elicit a percept.

Specifically, FIGS. 3A-3F demonstrate changes in phosphene shape observed with an increase in either stimulation amplitude or frequency for an electrode identified as M3. Each row of FIGS. 3A-3F represents a different set of stimulation parameters. The first row (FIGS. 3A and 3B) represents phosphene drawings at baseline parameters of 1.25×Th and 20 Hz, the second row (FIGS. 3C and 3D) increases amplitude to 4×Th and keeps frequency constant at 20 Hz, while the third row (FIGS. 3E and 3F) increases frequency to 80 Hz, keeping amplitude constant at 1.25×Th. The first column (FIGS. 3A, 3C and 3E) plots each trial for a given set of stimulation parameters in a different shade of grey at their drawn locations. The second column (FIGS. 3B, 3D and 3F) averages the trials from the first column at the mean centroid of the repeat measurements and plots the results in a grey-scaled image. Averaging of trials from FIGS. 3A, 3C and 3E are shown in FIGS. 3B, 3D and 3F respectively. Data from the first column visually demonstrate that phosphene characteristics are repeatable in spatial position and in shape across trials. Compared to baseline parameters (FIG. 3B), phosphene size visibly increases with an increase in amplitude (FIG. 3D), and does not visibly change with an increase in frequency (FIG. 3F).

FIG. 4 shows an exemplary set of size and brightness data across all nine separate electrodes, each in a different shade of grey, for all modulated amplitude (FIGS. 4A and 4C) and frequency (FIGS. 4B and 4D) conditions.

Figure 4A:
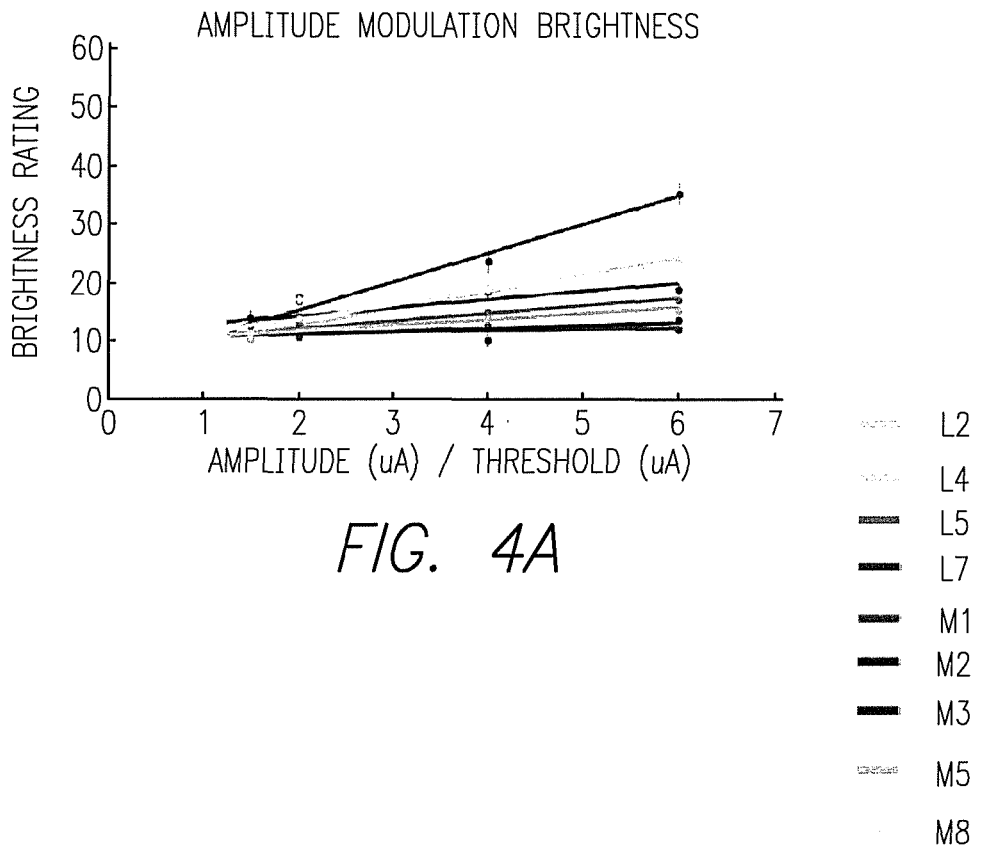
FIGS. 4A-4D show an exemplary set of graphs for brightness and size of percepts or phosphenes for nine separate electrodes, as shown in the legend.
Figure 4B:
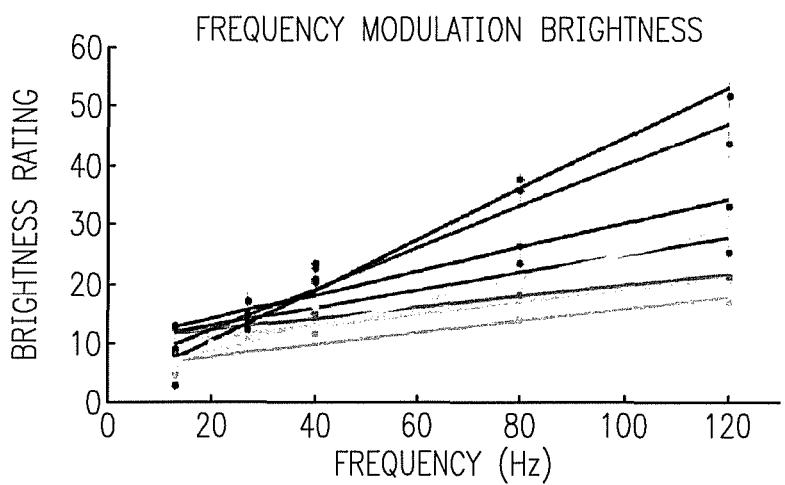
Figure 4C:
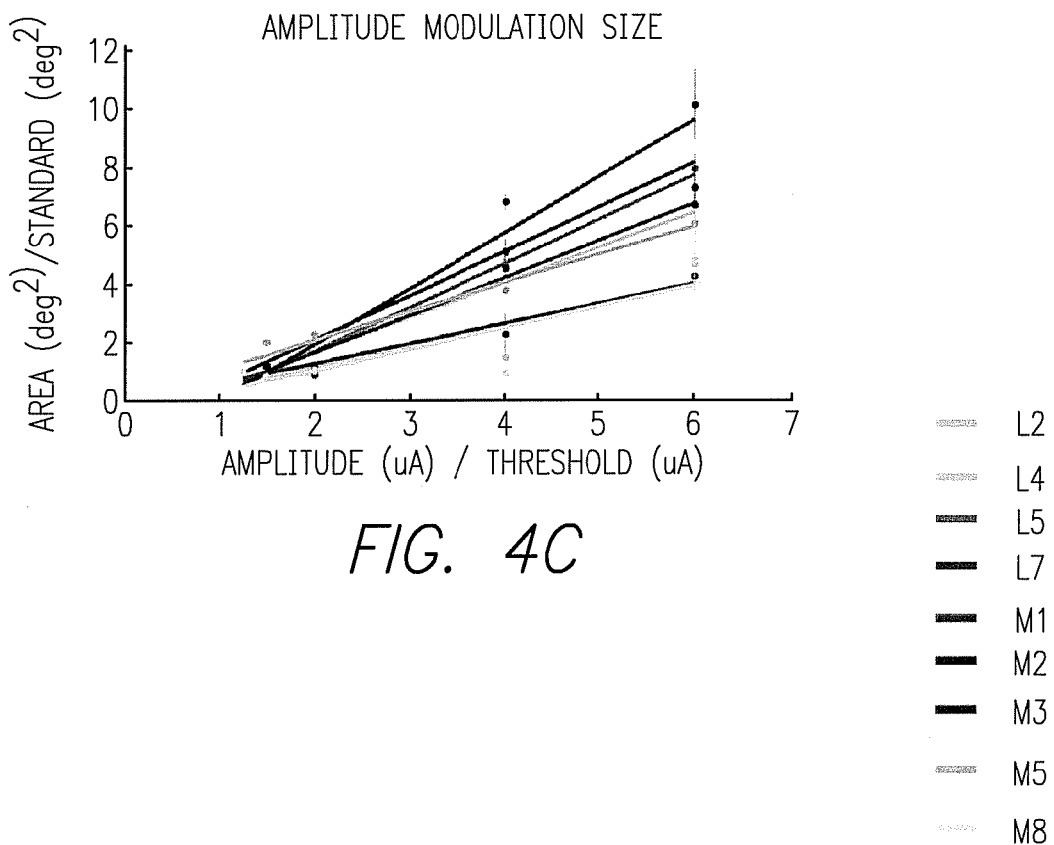
Figure 4D:
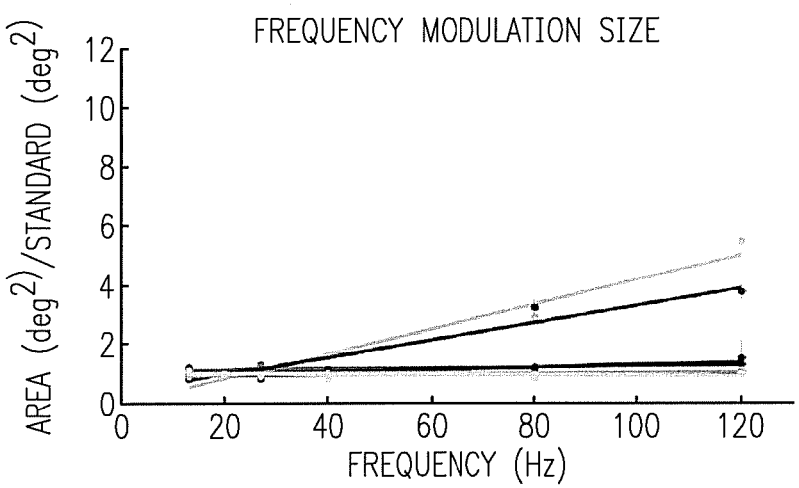
Figure 5A:
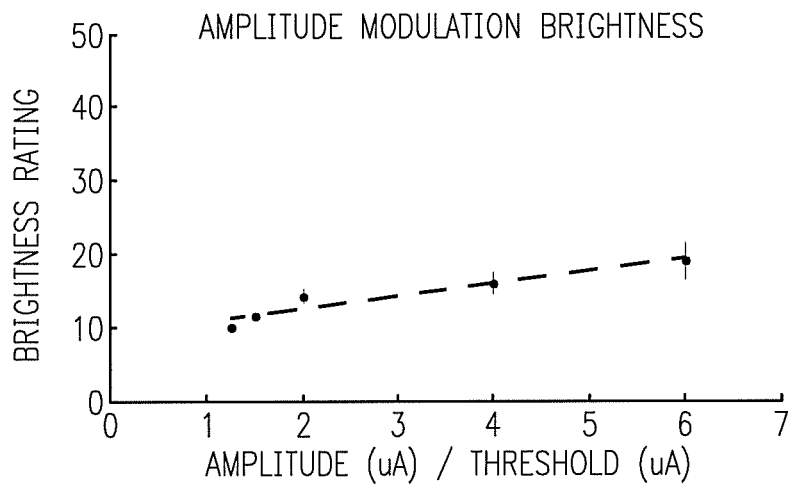
FIGS. 5A-5D show an exemplary set of graphs for average results from nine electrodes for brightness plotted as a function of amplitude (FIG. 5A), brightness plotted as a function of frequency (FIG. 5B), size plotted as a function of amplitude (FIG. 5C), and size plotted as a function of frequency (FIG. 5D).
Figure 5B:
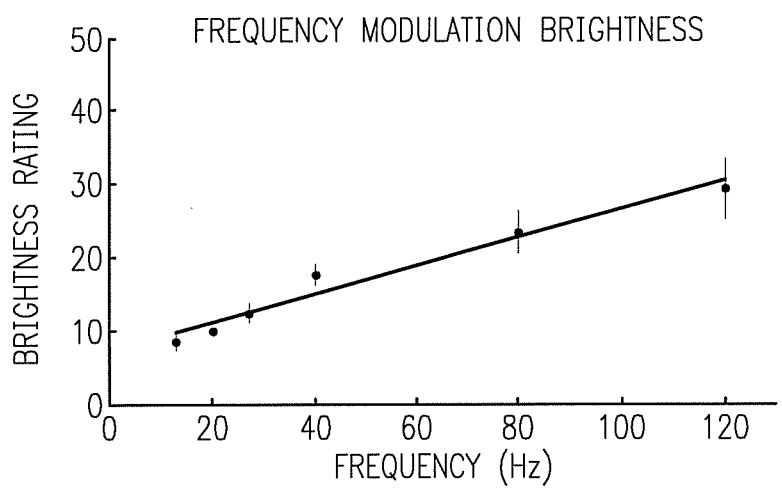
Figure 5C:
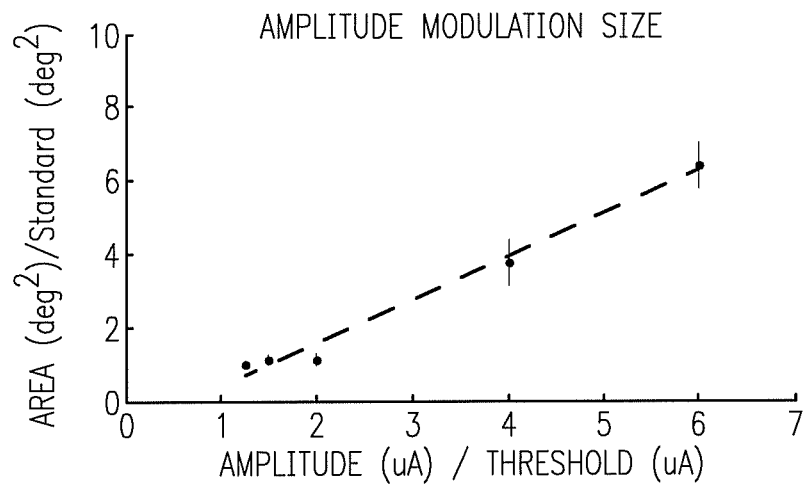
Figure 5D:
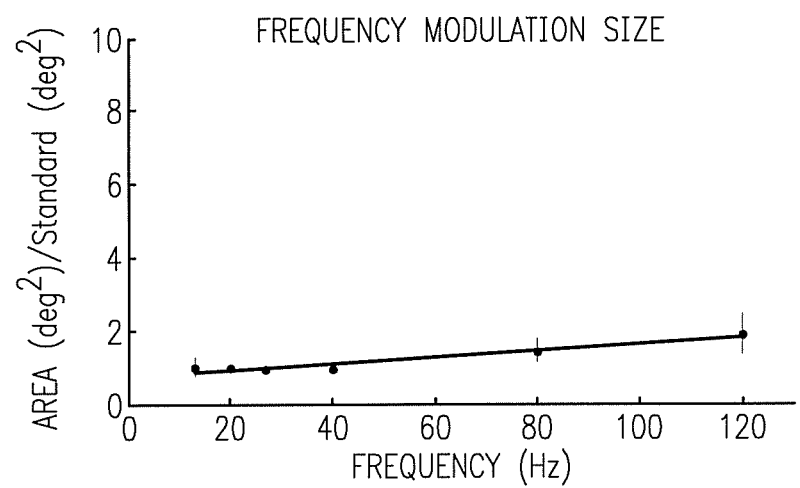

In amplitude plots, x-axes are normalized with respect to threshold parameters. In size plots, y-axes are normalized with respect to a standard (at 1.25×Th and 20 Hz). The straight lines on each plot are linear regression best-fit lines of the datasets. An increase in phosphene brightness or amplitude was indicated when the slope of the best-fit line was different from zero. In all nine electrodes, the size of the phosphenes increased as a function of amplitude (p<0.01 for all nine electrodes) as shown in FIG. 4C. Brightness increased with amplitude in seven out of nine electrodes as shown in FIG. 4A (p<0.01 for all seven cases). Apparent brightness increased as a function of frequency across all nine electrodes (FIG. 4B). In six out of nine electrodes, size did not vary with frequency (p>0.01). Although phosphene size statistically increased in three out of nine electrodes, in one case (electrode M2) the increase was very slight (FIG. 4D).

FIG. 5 shows exemplary plots of average brightness and size data across all electrodes. In FIGS. 5C and 5D, phosphene size is calculated relative to the mean phosphene at baseline parameters for each electrode and then averaged across all electrodes. Best-fit lines through the averaged data sets are again calculated using a linear regression model. Phosphene brightness increases with both amplitude and frequency coding (FIGS. 5A and 5B). Percept size grows by a factor of 6 with increasing amplitude from baseline (1.25× Th) to 6×Th (p<0.01) as shown in FIG. 5C. Percept size does not change (p>0.05) with an increase in frequency (FIG. 5D).

Exemplary phosphene or percept predictions, generated with the spatial sensitivity model 220 of FIG. 2, are shown in FIG. 6 for increasing amplitude (FIGS. 6A-6E) and increasing frequency (FIGS. 6F-6K). Note that the 1.25×Th at 20 Hz output is common to both the amplitude and frequency modulation rows.

All predictions yields a round and symmetrical percept due to the assumption of uniform current spread from a disc electrode. Calculating the predicted percept size revealed that amplitude modulation results in a growth in percept size by a factor of 7 while frequency modulation increased percept size by a factor of 1.3. Using the maximum value to calculate overall brightness, frequency modulation causes an increase in brightness by a factor of 4.9, while amplitude modulation increased brightness by a factor of 2.6.

FIG. 7A is an exemplary graph showing experimental results of average area and brightness of percepts at various amplitudes and frequencies of stimulation. FIG. 7B is an exemplary graph showing modeling predictions for average area and brightness of percepts at various amplitudes and frequencies of stimulation, the model derived by the results shown in FIG. 7A.

Referring to the results in FIG. 5, at each modulated amplitude and frequency condition, there is a single average brightness value and a corresponding average size measurement. In FIG. 7A, Applicants plot each experimental average brightness value against its corresponding size measurement for both the modulated amplitude and modulated frequency conditions. In FIG. 7B, Applicants plot model brightness vs. size based on percept predictions shown in FIG. 6. Computational modeling size and brightness predictions are shown to be comparable to experimental data for this embodiment of the present disclosure.

In both experimental and modeling (FIGS. 7A and 7B), the range of dynamic brightness levels is less in the modulated amplitude conditions (solid lines), than the modulated frequency condition (dashed lines). Furthermore, modulating amplitude causes a steep increase in phosphene size across the range of brightness levels for both experimental data and percept modeling. With frequency modulation (solid lines), predicted and experimental phosphene size increases with a shallow slope across the brightness levels.

Therefore, Applicants' experiments demonstrate that phosphene size and brightness are modulated by stimulation amplitude or frequency. Further, changes in size and brightness can be controlled independently. Applicants find that changes in phosphene appearance with either intensity (amplitude) or rate (frequency) coding can be predictably modeled based on the visual sensitivity properties of the retina and the spatial spread of current from a disc electrode from a previously published Perceptual Sensitivity Model discussed in reference 3. Phosphene size and brightness is dependent not only the amount of total charge in the stimulus pulse train but also the distribution of charge within that pulse train.

The examples set forth above are provided to give those of ordinary skill in the art a complete disclosure and description of how to make and use the embodiments of the present disclosure, and are not intended to limit the scope of what the inventors regard as their disclosure. Modifications of the above-described modes for carrying out the disclosure may be used by persons of skill in the art, and are intended to be within the scope of the following claims. All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. For example, the person skilled in the art will understand that the number steps or components shown is only indicative and that the method can occur in more or fewer steps and that the system may contain more or less components according to the various embodiments. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

REFERENCES

1. Mahadevappa M, Weiland J D, Yanai D, Fine I, Greenberg R J, Humayun M S. Perceptual thresholds and electrode impedance in three retinal prosthesis subjects. IEEE Trans Neural Syst Rehabil Eng 2005; 13:201-206.
2. de Balthasar C, Patel S, Roy A, et al. Factors affecting perceptual thresholds in epiretinal prostheses. Invest Ophthalmol Vis Sci 2008; 49:2303-2314.
3. Horsager A, Greenwald S H, Weiland J D, et al. Predicting visual sensitivity in retinal prosthesis patients. Invest Ophthalmol Vis Sci 2009; 50:1483-1491.
4. Greenwald S H, Horsager A, Humayun M S, Greenberg R J, McMahon M J, Fine I. Brightness as a function of current amplitude in human retinal electrical stimulation. Invest Ophthalmol Vis Sci 2009; 50:5017-5025.
5. Nanduri D, Humayun M S, Greenberg R J, McMahon M J, Weiland J D. Retinal prosthesis phosphene shape analysis. Conf Proc IEEE Eng Med Biol Soc 2008; 2008:1785-1788.
6. Rizzo J F, 3rd, Wyatt J, Loewenstein J, Kelly S, Shire D. Perceptual efficacy of electrical stimulation of human retina with a microelectrode array during short-term surgical trials. Invest Ophthalmol Vis Sci 2003; 44:5362-5369.
7. Evans J R, Gordon J, Abramov I, Mladejovsky M G, Dobelle W H. Brightness of phosphenes elicited by electrical stimulation of human visual cortex. Sens Processes 1979; 3:82-94.
8. Dobelle W H, Mladejovsky M G. Phosphenes produced by electrical stimulation of human occipital cortex, and their application to the development of a prosthesis for the blind. J Physiol 1974; 243:553-576.
9. Brindley G S, Lewin W S. The visual sensations produced by electrical stimulation of the medial occipital cortex. J Physiol 1968; 194:54-55P.
10. Brindley G S, Donaldson P E, Falconer M A, Rushton D N. The extent of the region of occipital cortex that when stimulated gives phosphenes fixed in the visual field. J Physiol 1972; 225:57 P-58P.
11. Humayun M S, Prince M, de Juan E, Jr., et al. Morphometric analysis of the extramacular retina from postmortem eyes with retinitis pigmentosa. Invest Ophthalmol Vis Sci 1999; 40:143-148.
12. Stone J L, Barlow W E, Humayun M S, de Juan E, Jr., Milam A H. Morphometric analysis of macular photoreceptors and ganglion cells in retinas with retinitis pigmentosa. Arch Ophthalmol 1992; 110:1634-1639.
13. Ahuja A K, Behrend M R, Kuroda M, Humayun M S, Weiland J D. An in vitro model of a retinal prosthesis. IEEE Trans Biomed Eng 2008; 55:1744-1753.
14. Shannon R V. A model of threshold for pulsatile electrical stimulation of cochlear implants. Hear Res 1989; 40:197-204.
15. Chander D, Chichilnisky E J. Adaptation to temporal contrast in primate and salamander retina. J Neurosci 2001; 21:9904-9916.
16. Rieke F. Temporal contrast adaptation in salamander bipolar, cells. J Neurosci 2001; 21:9445-9454.

17. Watson A B. Temporal Sensitivity. In: Boff K R, Kaufman L, Thomas J P (eds), Handbook of perception and human performance. New York: Wiley; 1986.

The invention claimed is:

1. A method of stimulating perception of vision with a visual prosthesis comprising adjusting percept size by adjusting amplitude and adjusting percept brightness by adjusting frequency of a stimulation signal of at least one electrode of the visual prosthesis.

2. The method according to claim 1, further comprising utilizing a model to adjust the percept size and percept brightness in concert by adjusting frequency and amplitude of the stimulation signal of at least one electrode of the visual prosthesis.

3. The method according to claim 2, wherein the percept size is adjusted without changing the percept brightness.

4. A method for adjusting size and brightness of a percept independently, comprising:
   providing a visual prosthesis with at least one electrode;
   stimulating the at least one electrode with a pulsed electrical signal to elicit a percept;
   adjusting amplitude of the pulsed electrical signal applied to at least one electrode and measuring resulting percept size and brightness;
   adjusting frequency of the pulsed electrical signal applied to at least one electrode and measuring resulting percept size and brightness;
   deriving a model of the resulting percept size and brightness from the adjusting of amplitude and frequency; and
   utilizing the model to adjust the amplitude and frequency of the pulsed electrical signal for stimulating the at least one electrode to elicit a percept of a controlled size and brightness.

5. The method according to claim 4, wherein the deriving of the model comprises:
   applying a spatial attenuation function to the pulsed electrical signal to produce a spatio-temporal stimulus profile;
   adjusting a filter time constant, a suprathreshold desensitization constant and a power non-linearity to fit current integration and desensitization behavior of the measured percept size and brightness due to adjustments in amplitude and frequency independently;
   applying a sigmoidal function to the adjusted signal;
   applying a slow integrator; and
   determining the size and brightness of the percept as a function of the amplitude and frequency of the pulsed electrical signal.

6. The method according to claim 4, further comprising adjusting the amplitude or frequency of each electrode depending on the ganglion cell density next to the electrode.

7. The method according to claim 4, further comprising adjusting the shape of the percept based on shape fitting of the visual prosthesis.

8. A visual prosthesis comprising:
   an array of electrodes configured for placement in proximity of a visual neural tissue;
   a neural stimulator, coupled to the array of electrodes and adapted for applying stimuli through the array of electrodes to visual neural tissue to elicit percepts;
   a control device, coupled to the neural stimulator and adapted for controlling amplitude of the stimuli, and controlling frequency of the stimuli independently of the amplitude of the stimuli and
   a computing device, coupled to the control device and adapted for deriving a model for size and brightness of each percept as a function of the amplitude and frequency of the stimuli,
   wherein the control device is further adapted for adjusting the amplitude and frequency of the stimuli based on the model to elicit at least one percept of an expected size and brightness.

9. The visual prosthesis according to claim 8, wherein the control device is further adapted to adjust percept size without changing the brightness.

10. The visual prosthesis according to claim 8, wherein the control device is further adapted to adjust percept brightness without changing the size.

11. The visual prosthesis according to claim 8, wherein the model is a spatial sensitivity model.

12. The visual prosthesis according to claim 8, wherein the model predicts the size and brightness of percepts based on total charge of stimulus pulse train and distribution of charge within the stimulus pulse train.

13. The visual prosthesis according to claim 8, wherein the model predicts the size and brightness of percepts based on total charge of stimulus pulse train and distribution of charge within the stimulus pulse train.

14. The visual prosthesis according to claim 8, wherein the control device is further adapted to adjust the shape of the percept based on shape fitting of the visual prosthesis.

15. A device for controlling a visual prosthesis, comprising:
   means for controlling amplitude and frequency of stimuli to be applied to visual neural tissue by the visual prosthesis;
   means for deriving a model for adjusting the amplitude and frequency of the stimuli based on desired percept size and brightness; and
   means for applying the model to adjust the amplitude and frequency of the stimuli to be applied based on the desired percept size and brightness.

16. The device according to claim 15, wherein the means for applying the model to adjust the amplitude and frequency can be used to adjust resulting percept size without changing the brightness.

17. The device according to claim 15, wherein the means for applying the model to adjust the amplitude and frequency can be used to adjust resulting brightness without changing the size.

18. The device according to claim 15, wherein the model is a spatial sensitivity model.

19. The device according to claim 15, wherein the model predicts the size and brightness of percepts based on total charge of stimulus pulse train and distribution of charge within the stimulus pulse train.

20. The device according to claim 15, further comprising means for adjusting the shape of the percept based on shape fitting of the visual prosthesis.

* * * * *